United States Patent [19]
Weitz et al.

[11] 4,042,587
[45] Aug. 16, 1977

[54] 1,2,4-DIHYDROTRIAZINE-4-OXIDES AND A PROCESS FOR THEIR PRODUCTION

[75] Inventors: Hans-Martin Weitz, Bad Durkheim; Rolf Fischer, Heidelberg; Dieter Lenke, Ludwigshafen, all of Germany

[73] Assignee: BASF Aktiengesellschaft, Ludwigshafen, Germany

[21] Appl. No.: 691,225

[22] Filed: June 1, 1976

[30] Foreign Application Priority Data

June 20, 1975 Germany ............................. 2527490

[51] Int. Cl.² ........................................... C07D 253/08
[52] U.S. Cl. .................................... 544/183; 424/249
[58] Field of Search .................................. 260/248 AS

[56] References Cited

U.S. PATENT DOCUMENTS 3,910,909 10/1975 Draber et al. ................ 260/248 AS

*Primary Examiner*—John M. Ford
*Attorney, Agent, or Firm*—Keil, Thompson & Shurtleff

[57] ABSTRACT

New 1,2,4-dihydrotriazine-4-oxides and a new process for the manufacture of 1,2,4-dihydrotriazine-4-oxides by reaction of oximino-cycloalk-1-enes, which are substituted in the 1-position, with hydrazine and ketones. The compounds I are pesticides and starting materials for the manufacture of pesticides.

7 Claims, No Drawings

1,2,4-DIHYDROTRIAZINE-4-OXIDES AND A PROCESS FOR THEIR PRODUCTION

The present invention relates to the new 1,2,4-dihydrotriazine-4-oxides and to a new process for the manufacture of 1,2,4-dihydrotriazine-4-oxides by reaction of oximino-cycloalk-1-enes which are substituted in the 1-position, with hydrazine and ketones.

It is known that the oxidation of substituted 1,2,4-triazines yields 1,2,4-triazine-1-oxides (J. Org. Chem. 36 (1971), 787–790), while 1,2,4-triazine-4-oxides cannot be prepared by this method.

It is an object of the present invention to provide a new process for the manufacture of 1,2,4-dihydrotriazine-4-oxides by a one-step reaction, in a simple and economical manner and in good yield and high purity.

The new 1,2,4-dihydrotriazine-4-oxides are a further object of the present invention.

We have found that these objects are achieved and that 1,2,4-dihydrotriazine-4-oxides of the formula

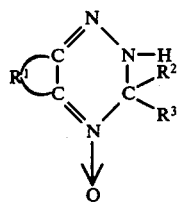

I, where $R^1$ is an aliphatic radical, and $R^2$ and $R^3$ are identical or different and each is an aliphatic, cycloaliphatic, araliphatic or aromatic radical, or $R^2$ and $R^3$ together with the adjacent carbon are members of an alicyclic ring, are obtained in an advantageous manner when oximino-cyloalk-1-enes which are substituted in the 1-position, of the formula

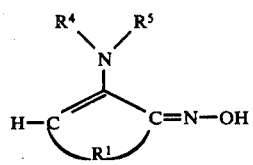

II, where $R^4$ and $R^5$ are identical or different and each is an aliphatic radical, or $R^4$ and $R^5$ together with the adjacent nitrogen are members of a heterocyclic ring, and $R^1$ is an aliphatic radical, are reacted with ketones of the formula

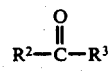

III, where $R^2$ and $R^3$ have the above meanings, and with hydrazine, in organic solvents which are inert under the reaction conditions.

Further, we have found the new 1,2,4-dihydrotriazine-4-oxides of the formula

I,

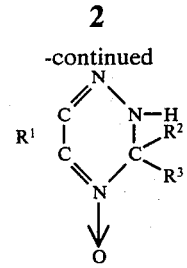

where $R^1$ is an aliphatic radical and $R^2$ and $R^3$ may be identical or different and each is an aliphatic, cyloaliphatic, araliphatic or aromatic radical or $R^2$ and $R^3$ together with the adjacent carbon are members of an alicyclic ring.

Where 1-morpholino-6-oximino-cyclohex-1-ene and acetone are used, the reaction can be represented by the following equation:

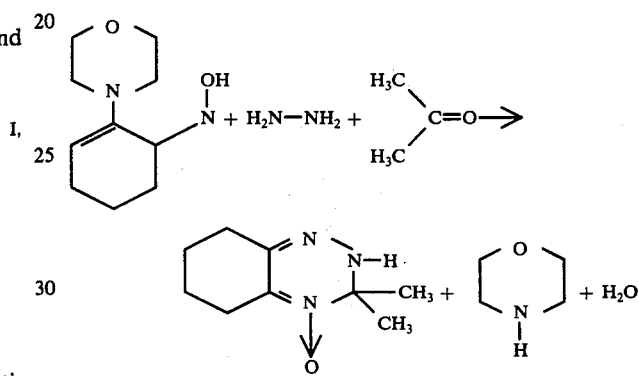

The process of the invention gives 1,2,4-dihydrotriazine-4-oxides in a one-step reaction, in a simple and economical manner and in good yield and high purity.

Preferred starting materials II and III and, accordingly, preferred end products I are those where $R^1$ is alkylene of 2 to 10 carbon atoms, $R^2$ and $R^3$ are identical or different and each is alkyl of 1 to 8 carbon atoms, cycloalkyl of 5 to 8 carbon atoms, aralkyl of 7 to 12 carbon atoms or phenyl or $R^2$ and $R^3$ together with the adjacent carbon are members of a 5-membered to 13-membered alicyclic ring, and $R^4$ and $R^5$ are identical or different and each is alkyl of 1 to 8 carbon atoms or $R^4$ and $R^5$ together with the adjacent nitrogen are members of a 5-membered or 6-membered heterocyclic ring which in addition to the said nitrogen may contain a further nitrogen, or an oxygen. The said radicals and rings may in addition be substituted by groups which are inert under the reaction conditions, eg. alkyl or alkoxy each of 1 to 4 carbon atoms.

The following cycloalkenes are examples of suitable starting materials II: 1-morpholino-5-oximino-cylopent-1-ene, 1-morpholino-6-oximino-cyclohex-1-ene, 1-morpholino-7-oximino-cyclohept-1-ene, 1-morpholino-8-oximino-cyclooct-1-ene, 1-morpholino-9-oximino-cyclonon-1-ene, 1-morpholino-10-oximino-cyclodec-1-ene, 1-morpholino-12-oximino-cyclododec-1-ene, 1-morpholino-18-oximino-cyclooctadec-1-ene, 1-morpholino-16-oximino-cyclohexadec-1-ene, 1-morpholino-17-oximino-cycloheptadec-1-ene, 1-morpholino-15-oximino-cyclopentadec-1-ene, 1-morpholino-14-oximino-cyclotetradec-1-ene, 1morpholino-11-oximino-cycloundec-1-ene and 1-morpholino-13-oximino-cyclotridec-1-ene; analogous 1-piperidino-, 1-pyrrolidino-, 1-piperazino-, 1-dimethylamino-, 1-diethylamino- 1-N-methyl-N-ethylamino-, 1-imidazolidino-, 1-pyrrolino-(Δ2')- and 1-imidazolo-oximino compounds and 1-di (methyl)-, 1-di(ethyl)-, 1-di-(n-propyl)-, 1-di-(isopropyl)-, 1-di-(n-butyl)-, 1-di(isobutyl)-, 1-di-(sec.-butyl), 1-di-(tert.-butyl)-, 1-di-(pentyl)-, 1-di-(pentyl-2')-, 1-di(pentyl-3')-, 1-di-(n-hexyl)-, 1-di-(n-heptyl)-, 1-di-(n-octyl)-, 1-di-(n-nonyl)-, 1-di-(n-decyl)-, 1-di-(2-ethylhexyl)-, 1-di-(2,2,6-trimethyl-n-heptyl)-, 1-di-(2-ethylpentyl)-, 1-di-(3-ethylpentyl)-, 1-di-(2,3-dimethyl-n-butyl)-, 1-di-(2,2-dimethyl-n-butyl)-, 1-di-(2-methylpentyl)-, 1-di(3-methylpentyl)-, 1-di-(2,2,4-trimethylheptyl)-, 1-di-(2-methylheptyl)-, 1-di-(3-methylheptyl)-, 1-di-(4-methylheptyl), 1-di-(3-ethylhexyl)-, 1-di-(2,2-dimethylhexyl)-, 1-di-(2,3-dimethylhexyl)-, 1-di-(2,4-dimethylhexyl)-, 1-di-(2,5-dimethylhexyl)-, 1-di-(3,3-dimethylhexyl)-, 1-di-(3,4-dimethylhexyl)-, 1-di-(2-methyl-3-ethylpentyl)-, 1-di-(3-methyl-3-ethylpentyl)-, 1-di-(2,2,3-trimethylpentyl)-, 1-di-(2,2,4-trimethylpentyl)-, 1-di-(2,3,3-trimethylpentyl)-, 1-di-(2,3,4-trimethylpentyl)-, and 1-di-(2,2,3,3-tetramethylbutyl)-oximino compounds; and corresponding oximino compounds containing 2 of the above radicals which are, however, different from one another, eg. the methylethyl-oximino compound.

The reaction is carried out with hydrazine, which is generally added in the form of hydrazine hydrate to the starting mixture. However, it is also possible to use hydrazine itself or its salts, eg. the primary or secondary sulfates. The reaction is carried out with hydrazine and the ketone in stoichiometric amount or in an excess, preferably with a ratio of from 1.1 to 1.5 moles of hydrazine and/or from 1 to 10 moles of ketone III per mole of starting material II. If the starting mixture still contains oxygen, it is advantageous to increase the amount of hydrazine accordingly.

Suitably ketones III are acetone, methyl ethyl ketone, methyl n-propyl ketone, methyl isopropyl ketone, methyl n-butyl ketone, methyl isobutyl ketone, methyl sec.-butyl ketone, methyl tert.-butyl ketone, methyl n-pentyl ketone, methyl pentyl-2 ketone, methyl pentyl-3 ketone, methyl isoamyl ketone, methyl (2-methyl)-butyl ketone, methyl (1-methyl)-butyl ketone, methyl (2-ethyl)-butyl ketone, methyl (3-ethyl)-butyl ketone, methyl (2,2-dimethyl)-butyl butyl ketone, methyl (2,3-dimethyl)-butyl ketone and methyl (3,3-dimethyl-butyl ketone; corresponding unsymmetrical ketones which in place of the methyl group contain the ethyl, n-propyl, isopropyl, n-butyl, isobutyl, sec.-butyl, tert.-butyl, n-pentyl, pentyl-2, pentyl-3, isoamyl, (2-methyl)-butyl, (1-methyl) -butyl, (2-ethyl)-butyl, (3-ethyl)-butyl, (2,2-dimethyl)-butyl, (2,3-dimethyl)-butyl or (3,3-dimethyl)-butyl group; diethyly ketone, di-n-propyl ketone, di-isopropyl ketone, di-n-butyl ketone, di-iso-butyl ketone, di-sec.-butyl ketone, di-tert.-butyl ketone, di-n-pentyl ketone, dipentyl-2 ketone, dipentyl-3 ketone, diisoamyl ketone, di-(2-methyl)-butyl ketone, di-(1-methyl)-butyl ketone, di-(2-ethyl)-butyl ketone, di-(3-ethyl)-butyl ketone, di-(2,2-dimethyl)-butyl ketone, di-(2,3-dimethyl)-butyl ketone and di-(3,3-dimethyl)-butyl ketone, dicyclohexyl ketone, dicyclopentyl ketone, dicycloheptyl ketone, dicyclooctyl ketone, dibenzyl ketone, diphenylethyl ketone, diphenyl ketone, diphenylpropyl ketone, di-(o-hydroxy-phenylethyl) ketone, di-(m-hydroxyphenylethyl) ketone and di-(p-hydroxyphenylethyl) ketone; di-(2-methyl-phenyl) ketone, di-(3-methyl-phenyl) ketone, di-(4-methyl-phenyl) ketone, di-(2-ethyl-phenyl) ketone, di-(3-ethyl-phenyl) ketone, di-(4-ethyl-phenyl) ketone, di-(2-propyl-phenyl) ketone, di-(3propyl-phenyl) ketone, di-(4-propyl-phenyl) ketone, di-(2-butyl-phenyl) ketone, di-(3-butyl-phenyl) ketone, di-(4-butyl-phenyl) ketone, di-(2-isopropyl-phenyl) ketone, di-(3-isopropyl-phenyl) ketone, di-(4-isopropyl-phenyl) ketone, di-(2-hydroxy-phenyl) ketone, di-(3-hydroxy-phenyl) ketone, di-(4-hydroxy-phenyl) ketone, di-(2-methoxy-phenyl) ketone, di-(3-methoxy-phenyl) ketone, di-(4-methoxy-phenyl) ketone, di-(2-ethoxy-phenyl) ketone, di-(3-ethoxy-phenyl) ketone, di-(4-ethoxy-phenyl) ketone, di-(2,3-dimethyl-phenyl) ketone, di-(2,4-dimethyl-phenyl) ketone, di-(2,6-dimethyl-phenyl) ketone, di-(3,5-dimethyl-phenyl) ketone, di-(2,3-diethyl-phenyl) ketone, di-(3,4-diethyl-phenyl) ketone, di-(2,6-diethyl-phenyl) ketone, di-(3,5-diethyl-phenyl) ketone, di-(2,3-dimethoxy-phenyl) ketone, di-(3,4-dimethoxy-phenyl) ketone, di-(2,6-dimethoxy-phenyl) ketone and di-(3,5-dimethoxy-phenyl) ketone; corresponding ketones wherein $R^2$ and $R^3$ have the above meanings but are different from one another, eg. 2-methyl-heptanone-6 and 4-(p-hydroxyphenyl)-butanone-2; and cyclopentanone, cyclohexanone, cycloheptanone, cylooctanone, cyclononanone, cyclodecanone, cycloundecanone, cyclododecanone and cyclotridecanone.

The reaction is in general carried out at from 20° to 200° C, preferably from 30° to 90° C, under atmospheric or superatmospheric pressure, and batchwise or continuously. Examples of suitable solvents are aromatic hydrocarbons, e.g. toluene, ethylbenzene, o-xylene, m-xylene, isopropylbenzene and methylnaphthalene, halohydrocarbons, expecially chlorohydrocarbons, e.g. amyl chloride, cyclohexyl choride, dichloropropane, methylene chloride, dichlorobutane, isopropyl bromide, n-propyl bromide, butyl bromide, chloroform, ethyl iodide, propyl iodide, chloronaphthalene, dichloronaphthalene, carbon tetrachloride, tetrachloroethane, trichloroethane, trichloroethylene, pentachloroethane, o-difluorobenzene, m-difluorobenzene, p-difluorobenzene, 1,2-dichloroethane, 1,1-dichloroethane, n-propyl chloride, 1,2-cis-dichloroethylene, n-butyl chloride, sec.-butyl chloride, tert.-butyl chloride, isobutyl chloride, chlorobenzene, fluorobenzene, bromobenzene, iodobenzene, o-dichlorobenzene, p-dichlorobenzene, m-dichlorobenzene, o-dibromobenzene, p-dibromobenzene, m-dibromobenzene, o-chlorotoluene, m-chlorotoluene, p-chlorotoluene, 1,2,4-trichlorobenzene, 1,10-dibromodecane and 1,4-dibromobutane, alkanols and cycloalkanols, e.g. ethanol, n-butanol, isobutanol, tert.-butanol, cyclohexanol, propanol and methanol, ethers, e.g. ethyl propyl ether, methyl tert.-butyl ether, n-butyl ethyl ether, di-n-butyl ether, diisoamyl ether, dioxane, diisopropyl ether, anisole, phenetole, cyclohexyl methyl ether, diethyl ether, tetrahydrofuran and thioanisole; aliphatic or cycloaliphatic hydrocarbons, e.g. heptane, pinane, nonane, o-, m- and p-cymene, gasoline fractions of boiling range from 70° to 190° C, cyclohexane, methylcyclohexane, petroleum ether, decalin, pentane, hexane, naphtha, 2,2,4-trimethylpentane, 2,2,3-trimethylpentane, 2,3,3-trimethylpentane, octane and appropriate mixtures. The amount of solvent used is advantageously from 200 to 10,000% by weight, preferably from 200 to 1,000% by weight, based on starting material II.

The reaction can be carried out as follows: hydrazine hydrate and the ketone are slowly added to a solution of the starting material II and the mixture is kept at the reaction temperature for from 2 to 6 hours, e.g. heated under reflux. It is also possible to heat a solution of the starting material II, in one of the above solvents, to the boil and then slowly to add the hydrazine hydrate and heat the mixture under reflux for from 2 to 6 hours; finally, the ketone III is added to the solution and the mixture is again heated under reflux, for from 5 to 20 hours. The end product is then isolated in the conventional manner, e.g., by distilling the mixture and, if appropriate, recrystallizing the residue from one of the above solvents.

The compounds which may be manufactured by the process of the invention, expecially the triazine derivative described in Example 1, have antiphlogistic properties and are valuable starting materials for the manufacture of dyes and pharmaceuticals. The antiphlogistic action of the triazine derivatives was tested on the carrageenin-induced paw oedema in rats. The test substances, administered orally, reduce the inflammatory swelling brought about by sub-plantar injection of 0.1 ml of a 1 percent strength carrageenin solution.

The compounds I are also pesticides and valuable starting materials for the manufacture of other pesticides used, e.g., against scab, Phytophthora infectans, powdery mildew and aquatic weeds, and in combating weeds in Indian corn, vine, sugar cane, millet and cotton crops. End products I which are particularly suitable for this type of use are those where $R^1$, $R^2$ and $R^3$ have the above preferred meanings, and especially those obtained from the individual starting materials II mentioned as being particularly suitable.

In the Examples which follow, parts are by weight.

EXAMPLE 1

3,3-Dimethyl-2,3,5,6,7,8,-hexahydro-1,2,4-benzo-triazine-4-oxide 78.4 parts of 1-morpholino-6-oximino-cyclohex-1-ene in 400 parts of ethanol are heated with 20 parts of hydrazine hydrate for 2 hours under reflux and 46.4 parts of acetone are added. The reaction mixture is kept for 20 hours at 78° C. After cooling and filtering the mixture, 42 parts of 3,3-dimethyl-2,3,5,6,7,8,-hexahydro-1,2,4-benzo-triazine-4-oxide of melting point 119° C (after recrystallization from acetone) are obtained; yield, 58% of theory.

EXAMPLES 2 TO 8

98 parts of 1-morpholino-6-oximino-cyclohex-1-ene are reacted with hydrazine hydrate and various ketones in the manner described in Example 1. The conditions and results may be seen from the Table which follows.

TABLE

| Example | Ketone | Parts of Ketone | Parts of hydrazine hydrate | End product | | Melting point (° C) | Yield (% of theory) |
|---|---|---|---|---|---|---|---|
| 2 | methyl cyclohexyl ketone | 230 | 25 | $R^2=CH_3$ $R^3=$ —⌬ (cyclohexyl) | | 138.5–139 | 44 |
| 3 | dibenzyl ketone | 105 | 25 | $R^2=CH_2-C_6H_5$ $R^3=CH_2-C_6H_5$ | | 159–161 | 48 |
| 4 | 2-methyl-heptanone-6 | 64 | 25 | $R^2=-CH_3$ $R^3=(CH_2)_3-CH(CH_3)_2$ | | 94–95 | 35 |
| 5 | 4-(p-hydroxyphenyl)-butanone-2 | 82 | 25 | $R^2=CH_3$ $R^3=(CH_2)_2-$C_6H_4-OH | | 167 | 53 |
| 6 | cyclopentanone | 210 | 25 | $R^2 + R^3 = (CH_2)_4$ | | 104–106 | 24 |
| 7 | cyclohexanone | 245 | 25 | $R^2 + R^3 = (CH_2)_5$ | | 170–171 | 62 |
| 8 | cyclodecanone | 91 | 25 | $R^2 + R^3 = (CH_2)_{11}$ | | 154–155 | 49 |

We claim:

1. 1,2,4-Dihydrotriazine-4-oxides of the formula

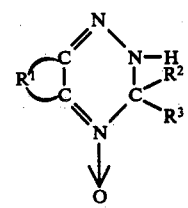

I, wherein $R^1$ is an alkylene of 2 to 10 carbon atoms, $R^2$ and $R^3$ are identical or different and each is alkyl of 1 to 8 carbon atoms cycloalkyl of 5 to 8 carbon atoms, aralkyl of 7 to 12 carbon atoms or phenyl or $R^2$ and $R^3$ together with the adjacent carbon are members of a 5-membered to 13 membered alicyclic ring.

2. A process for the manufacture of an 1,2,4-dihydrotriazine-4-oxide of the formula

I

-continued

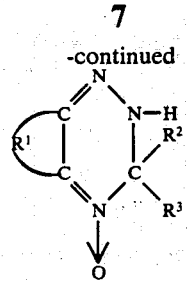

wherein $R^1$ is an alkylene of 2 to 10 carbon atoms, $R^2$ and $R^3$ are identical or different and each is alkyl of 1 to 8 carbon atoms, cycloalkyl of 5 to 8 carbon atoms, aralkyl of 7 to 12 carbon atoms or phenyl or $R^2$ and $R^3$ together with the adjacent carbon are members of a 5-membered to 13-membered alicyclic ring, wherein the said radicals and rings may in addition be substituted by alkyl or alkoxy each of 1 to 4 carbon atoms, in which oximino-cycloalk-1-enes which are substituted in the 1-position, of the formula

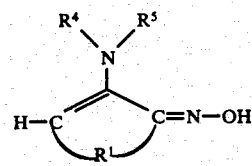

II, wherein $R^4$ and $R^5$ are identical or different and each is an alkyl of 1 to 8 carbon atoms or $R^4$ and $R^5$ together with the adjacent nitrogen are members of a 5-membered or 6-membered heterocyclic ring which in addition to the said nitrogen may contain a further nitrogen, or an oxygen, wherein the said radicals and rings may in addition be substituted by alkyl or alkoxy each of 1 to 4 carbon atoms, and $R^1$ has the above meaning, are reacted with ketones of the formula

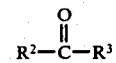

III, wherein $R^2$ and $R^3$ have the above meanings, and with hydrazine, in organic solvents which are inert under the reactions conditions.

3. A process as set forth in claim 2, in which the reaction is carried out with a ratio of from 1.1 to 1.5 moles of hydrazine and/or from 1 to 10 moles of ketone II per mole of starting material II.

4. A process as set forth in claim 2, in which the reaction is carried out at from 20° to 200° C.

5. A process as set forth in claim 2, in which the reaction is carried out at from 30° to 90° C.

6. A process as set forth in claim 2, in which the reaction is carried out in the presence of a solvent in amounts of from 200 to 10,000% by weight, based on starting material II.

7. A process as set forth in claim 2, in which the reaction is carried out in the presence of an aromatic hydrocarbon, halohydrocarbon, alkanol, cycloalkanol, ether or aliphatic or cycloaliphatic hydrocarbon.

* * * * *